US00PP12701P2

(12) United States Plant Patent
Yamamoto

(10) Patent No.: US PP12,701 P2
(45) Date of Patent: Jun. 11, 2002

(54) *HYDRANGEA MACROPHYLLA* NAMED 'YELLOWLEAF'

(75) Inventor: Takeomi Yamamoto, Tokyo (JP)

(73) Assignee: Hines Horticulture, INC, Irvine, CA (US)

( * ) Notice: Subject to any disclaimer, the term of this patent is extended or adjusted under 35 U.S.C. 154(b) by 0 days.

(21) Appl. No.: 09/490,863

(22) Filed: Jan. 24, 2000

(51) Int. Cl.[7] ..... A01H 5/00
(52) U.S. Cl. ..... Plt./250
(58) Field of Search ..... Plt./250

*Primary Examiner*—Bruce R. Campell
*Assistant Examiner*—Annette H. Para
(74) *Attorney, Agent, or Firm*—Christie, Parker & Hale, LLP

(57) ABSTRACT

A new plant variety of *Hydrangea macrophylla* characterized by its foliage color, which is bright golden yellow to chartreuse.

3 Drawing Sheets

BACKGROUND OF THE INVENTION

The present invention relates to a new and distinct variety of *Hydrangea macrophylla* (Thunb.) Ser., which was discovered as a branch sport in a controlled planting of *Hydrangea macrophylla* (unnamed, unpatented) in Shizuoka Prefecture, Japan. The varietal denomination of the new variety is 'YELLOWLEAF'.

The genus Hydrangea is included in the family Saxifragaceae which comprises about 80 genera and 1,200 species of herbs, shrubs, small trees, woody climbers mostly temperate in origin. Hydrangea comprises approximately 23 species of deciduous or evergreen shrubs and vines originating in North America, South America and East Asia, many of which possess desirable ornamental characteristics. Recent taxonomical treatments sometimes isolate Hydrangea in a new family, Hydrangeaaceae.

*Hydrangea macrophylla* is widespread and common throughout much of Japan. It generally has opposite, simple leaves, obovate to elliptic in shape, 10 to 20 cm long and 5 to 15 cm wide. Leaf color ranges from light to dark green, depending on light intensity and cultural conditions. Leaves are generally softly pubescent. Flower color is depended upon the pH level of the soil and the amount of available aluminum in the soil media. Flowers of *Hydrangea macrophylla* are borne in mostly sterile florets, formed in what is often called a "hortensia" flower.

SUMMARY OF THE INVENTION

The new variety exhibits golden yellow to chartreuse foliage throughout the growing season. Asexual reproduction of the new variety by stem cuttings performed in Tokyo, Japan; Lewisberry, Pa.; Vacaville, Calif.; and Fulshear, Tex.; has confirmed that the distinctive characteristics of the new variety are stable and transmitted to succeeding generations, and the new variety reproduces true to type.

COMPARISON WITH PLANT

'YELLOWLEAF' is distinguished from its parent and all other varieties of *Hydrangea macrophylla* of which I am aware by its foliage color, which is bright golden yellow to chartreuse.

BRIEF DESCRIPTION OF ILLUSTRATIONS

The accompanying illustrations show specimens of the new cultivar in photo illustrations as true to color as is reasonably possible to make in illustrations of this character. 'YELLOWLEAF' is shown with pink inflorescence grown under 75% shade, soil pH 6.4 and water pH of 6.4. Blue pigmentation of the inflorescence is also possible by manipulation of the nutrient amendments and pH of the growing medium.

DESCRIPTION OF THE NEW VARIETY

Figure 1:
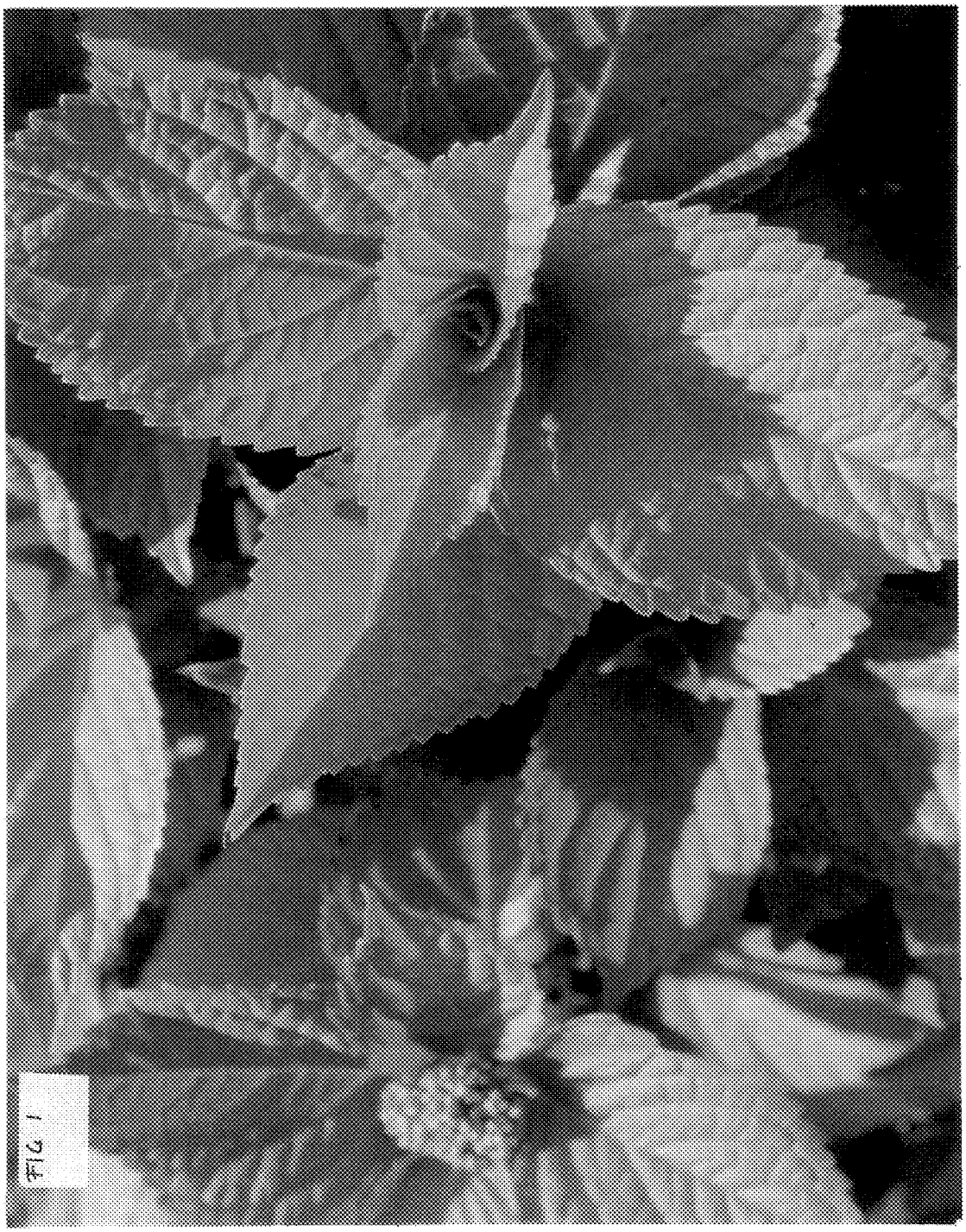
FIG. 1 shows the distinct yellow foliage coloration.
Figure 2:
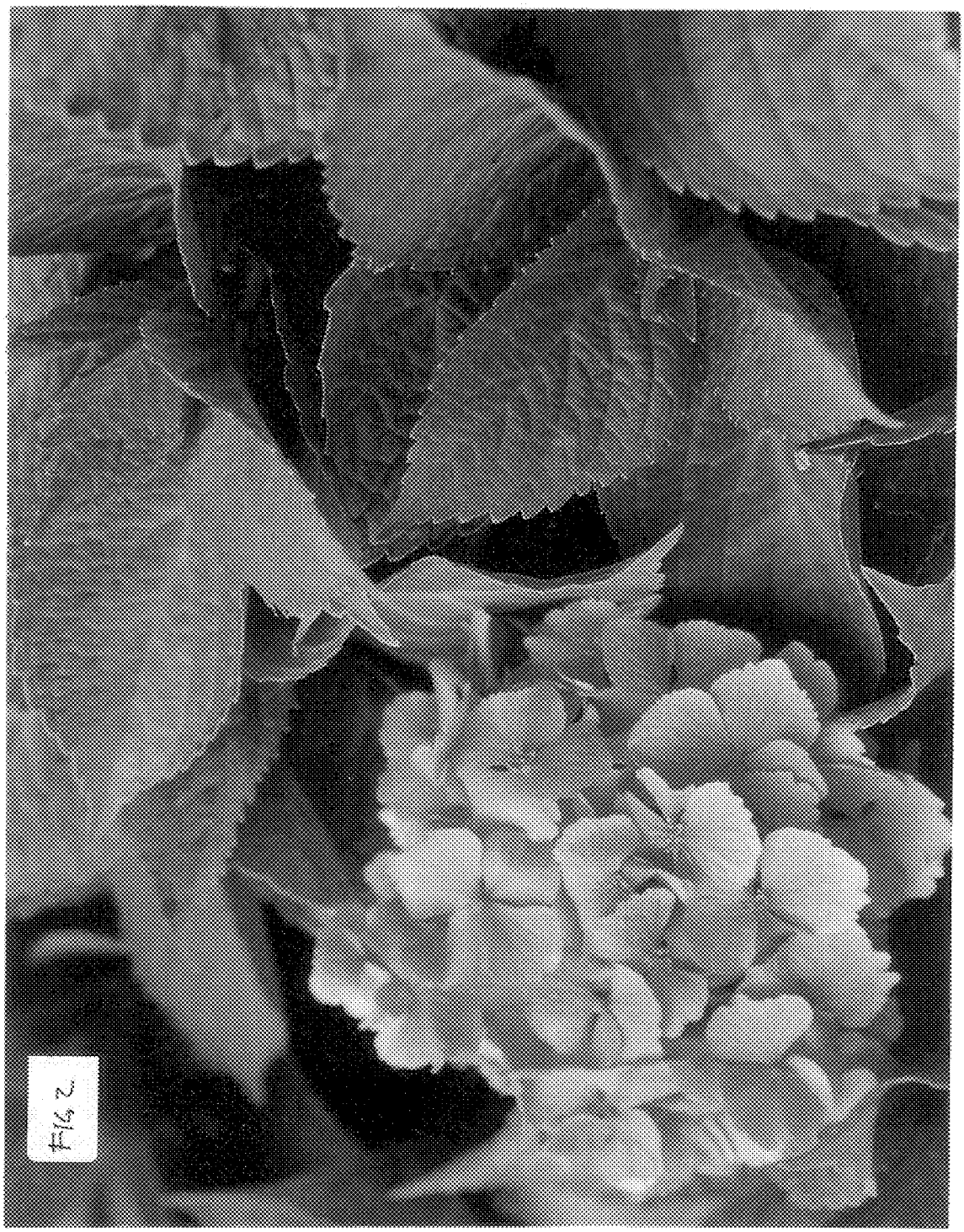
FIG. 2 illustrates the typical flower form with soil pH of 6.4 and water pH of 6.4.
Figure 3:
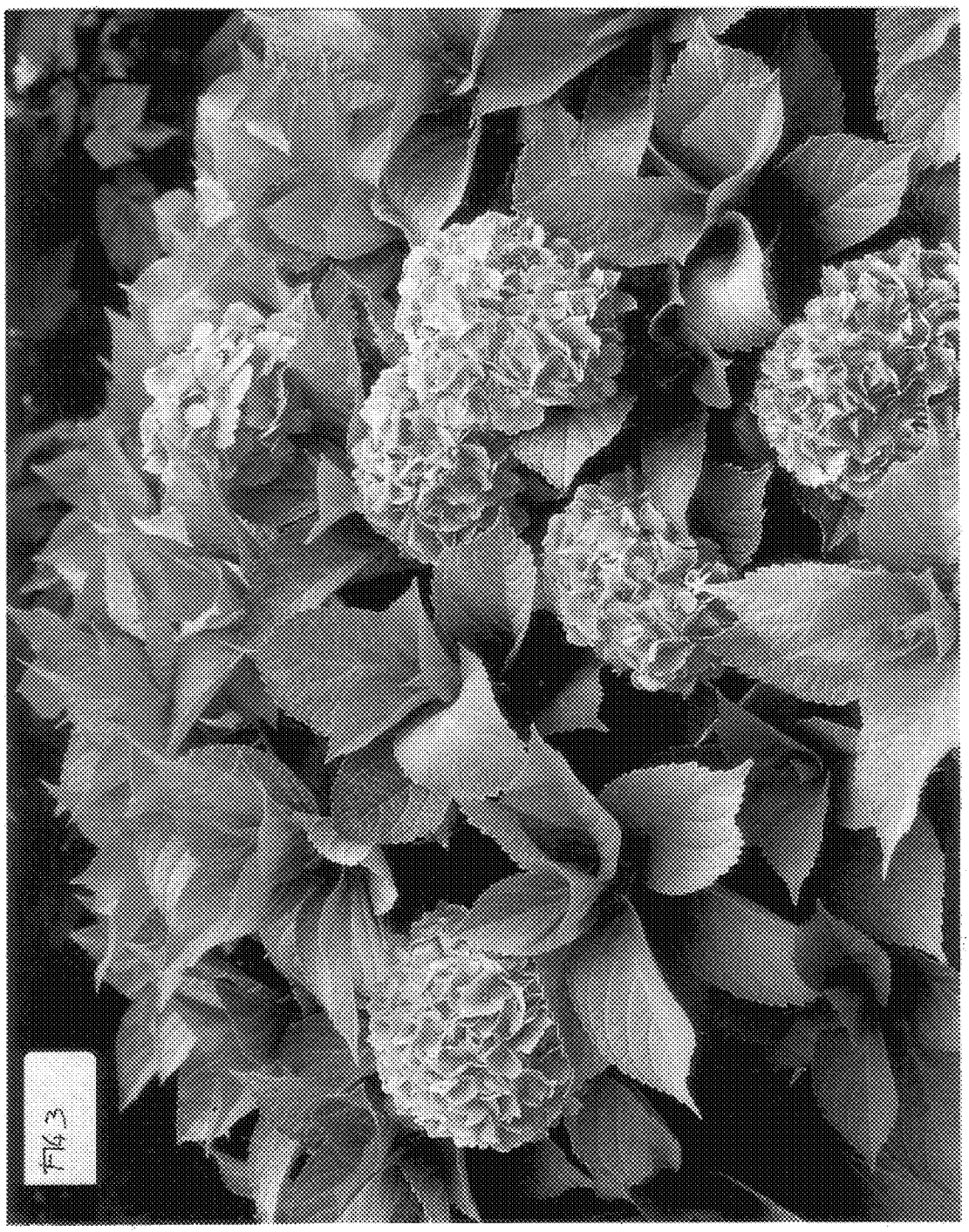
FIG. 3 illustrates the plants overall growth habit, the flower position on the plant, and the golden foliage coloration.

'YELLOWLEAF' has not been observed under all possible environmental, cultural, and light conditions. The following observations, descriptions and color readings are of 3-year-old plants grown in 5-gallon nursery containers under 75% shade at Vacaville, Calif. In the description, color references are to The Royal Horticultural Society Colour Chart (1995) and terminology used in the color descriptions herein refers to plate numbers in this color chart. Phenotypic expression may vary with light intensity, cultural, and environmental conditions.

Classification:

*Botanical.*—*Hydrangea macrophylla* (Thunb.) Ser. 'YELLOWLEAF'.

*Parentage.*—Branch sport of *Hydrangea macrophylla* (unnamed, unpatented).

*Propagation.*—By vegetative cuttings.

Plant:

*Size.*—Mature plant can grow to a height of about 1 meter.

*Habit.*—Upright, mound-forming deciduous shrub.

*Branching.*—Freely on 1-year-old wood.

Leaf:

*Shape.*—Ovoid.

*Base.*—Cuneate to obtuse.

*Apex.*—Acute to broadly acuminate.

*Size*.—As large as 16 cm long and 10.5 cm wide.

*Arrangement*.—Opposite.

*Margin*.—Serrate.

*Texture/substance*.—Thick; glabrous top and underside; veins prominent on the under side of the leaf and are furrowed on the leaf surface.

*Petioles*.—About 3.5 cm long. Color: Near Green Group 142C.

*Mature leaf color*.—Leaf color varies with intensity of sunlight and cultural conditions, color is generally yellow early in the growing season tending toward chartreuse. Upper side: Ranging from near Yellow Group 7B to 13C. Upper side: From near Green Group 143A to 143C (Shaded by flowers and other leaves). Under side: From near Green Group 143B to 143D (Covered by flowers and other leaves).

Stems:

*Thickness*.—7 to 10 cm.

*Texture*.—Smooth with raised lenticels.

*Internodes*.—About 7.5 cm.

*Hardiness*.—USDA Zone 6 (−10° F. to 0° F.).

*Vigor*.—Vigorous growth.

Inflorescence:

*Bloom period*.—Spring to Summer.

*Flower arrangement*.—Corymb, from about 100 to 200 florets per inflorescence, both sterile sepalous florets and fertile asepalous florets borne on the same panicle.

*Shape of inflorescence*.—Depressed globose.

*Flower form*.—3 to 5 irregularly, broadly obovate, petaloid sepals, toothed at the apex; sepals occasionally conjoined or overlapped.

*Flower size*.—About 20 cm.

*Sepals*.—Within each floret sepals differ in size, but with no clear pattern of size difference noted among florets.

*Color*.—Sepal color is near 62B at a soil pH of 6.4, however the sepals can be variable in color depending on soil pH and nutritional amendments supplied.

*Fragrance*.—None noted.

*Lastingness of individual blooms*.—Inflorescence is ornamental for 3 months; individual flowers of inflorescence last up to 15 days.

Reproductive system:

*Gynoecium*.—Stamens: None to 5. Pollen: White. Stigma: 1 to 4 per fertile flower.

*Fruit*.—Capsules, 0 to 4, ovoid to irregularly rounded when fully developed; less than 1 to 2 mm in diameter; near Brown Group 200B.

I claim:

1. A new plant variety of *Hydrangea macrophylla* of the variety substantially as shown and described.

* * * * *